United States Patent [19]
Nakayama et al.

[11] Patent Number: 5,625,911
[45] Date of Patent: May 6, 1997

[54] APPARATUS FOR SAMPLING URINE

[75] Inventors: Chiaki Nakayama; Kuniaki Shinohara; Naoki Sato; Hiroshi Tsuboi, all of Kita-kyushu, Japan

[73] Assignee: Toto Ltd., Fukuoka, Japan

[21] Appl. No.: 537,760

[22] PCT Filed: Feb. 23, 1995

[86] PCT No.: PCT/JP95/00259

§ 371 Date: Jan. 19, 1996

§ 102(e) Date: Jan. 19, 1996

[87] PCT Pub. No.: WO95/23337

PCT Pub. Date: Aug. 31, 1995

[30] Foreign Application Priority Data

Feb. 23, 1994 [JP] Japan .................................. 6-051289

[51] Int. Cl.⁶ .............................. E03D 11/00; A61B 5/00
[52] U.S. Cl. .............................................................. 4/661
[58] Field of Search ................................ 4/314, 420, 661;
128/760, 771

[56] References Cited

U.S. PATENT DOCUMENTS

| | | |
|---|---|---|
| 4,636,474 | 1/1987 | Ogura et al. . |
| 4,961,431 | 10/1990 | Ikenaga et al. . |
| 4,962,550 | 10/1990 | Ikegawa et al. . |
| 4,982,741 | 1/1991 | Saito et al. . |
| 5,073,500 | 12/1991 | Saito et al. . |
| 5,111,539 | 5/1992 | Hiruta et al. . |
| 5,184,359 | 2/1993 | Tsukamura et al. . |

FOREIGN PATENT DOCUMENTS

| | | |
|---|---|---|
| 59-217844 | 12/1984 | Japan . |
| 60-117155 | 6/1985 | Japan . |
| 60-233551 | 11/1985 | Japan . |
| 62-187253 | 8/1987 | Japan . |
| 1-136573 | 9/1989 | Japan . |
| 3-139334 | 6/1991 | Japan . |
| 5-30764 | 4/1993 | Japan . |
| 6-230006 | 8/1994 | Japan . |
| 6-258315 | 9/1994 | Japan . |
| 6-258316 | 9/1994 | Japan . |
| 7-35745 | 2/1995 | Japan . |

*Primary Examiner*—Charles E. Phillips
*Attorney, Agent, or Firm*—Finnegan, Henderson, Farabow, Garrett & Dunner, L.L.P.

[57] ABSTRACT

A method and an apparatus (30) for sampling urine at a toilet (10) equipped with a standard water closet bowl fixture (12). An elongated, curved, urine sampling trough (32) having a U-shaped cross-section is used. For sampling of urine, the sampling trough (32) is positioned in the vertical central plane (46) of the toilet bowl fixture in such a manner that it extends obliquely between the upper front region and the bottom region of the inner space of the bowl (14). As the urine sampling trough (32) covers a substantial length in the vertical direction as well as in the fore-and-aft direction, the urine column hits on the sampling trough even when the trajectory of urine column is fluctuated in the vertical or fore-and-aft direction, whereby urine is effectively sampled. As the urine sampling trough is elongated and curved, it can be readily stored under the toilet seat when not in use.

14 Claims, 6 Drawing Sheets

APPARATUS FOR SAMPLING URINE

TECHNICAL FIELD

The present invention relates to a method and an apparatus for in situ sampling urine excreted by the individuals at a toilet installed in residences, offices or other facilities to obtain urine sample for use in urine analysis. More specifically, the present invention relates to a method and an apparatus capable of sampling urine at a toilet equipped with a standardized water closet bowl fixture commercially available on the market.

BACKGROUND ART

In view of the trends for longevity of the individuals, the importance of health care and maintenance has been receiving increasing attention. As urine is an important source of information that represents the health conditions of an individual, various dysfunction such as pancreatic disorders (typically, diabetes), hypohepatia, and kidney disorders can be detected advantageously in a non-invasive manner by performing quantitative analysis of certain urine constituents, such as glucose, protein, urobilinogen, occult blood and other substances. Accordingly, proposed in the art are toilets having a urinalysis function which are capable of performing sampling and analysis of urine so as to assist the individuals in rendering their health check by making use of toilets provided in residences, offices and other facilities.

For instance, JP-A-59-217844 of Toto Ltd., U.S. Pat. Nos. 4,961,431 to Ikenaga et al., 4,962,550 to Ikenaga et al., 4,982,741 to Saito et al., 5,073,500 to Saito et al., 5,111,539 to Hiruta et al., and 5,184,359 to Tsukamura et al., propose to form a urine sampling cavity or sampling well on the bowl surface of a water closet bowl fixture to sample a quantity of urine excreted into the toilet bowl. The urine specimen thus sampled is subjected to urinalysis by way of liquid chromatographic process, colorimetric analysis process, or polarographic or voltammetric process.

The advantage of these sampling systems which are designed to make use of the urine sampling cavity or sampling well formed on the bowl surface is that urine excreted into the toilet bowl is received and collected by a considerably wide surface area of the bowl so that urine is readily sampled regardless of the direction of urination or the variation in the trajectory of urine column. Therefore, an adequate quantity of urine necessary for urinalysis can easily be sampled even in the case of elderly people who are apt to suffer from the shortage of the amount of urine per urination.

However, the problem associated with these systems is that they require a special-purpose toilet bowl fixture provided with a urine sampling cavity or well formed on the bowl surface for the purposes of sampling of urine so that a standard-type toilet bowl fixture having the conventional bowl configuration cannot be used. Accordingly, in order to sample urine and perform urinalysis at a toilet of residence, office or other facility, the existing conventional bowl fixture must first be removed and then a special purpose bowl fixture envisioned for sampling and urinalysis must be installed. This involves a great deal of labor and expenses for reform works and necessitates to discard the existing bowl fixture.

Furthermore, as such special purpose toilet bowl fixtures must be manufactured specially and separately from standard-type toilet bowls, it is difficult to produce them via the mass production process. As a result, these systems are too expensive to be installed widely in regular households and offices.

Another disadvantage is the difficulty in obtaining a good urine specimen since residual flushing water remaining in the urine sampling cavity of the bowl surface after flushing of the bowl tends to dilute the fresh urine to be sampled. Similarly, the fresh urine sample is susceptible to contamination by residual urine and feces since the urine sampling section is formed on the bowl surface.

In FIG. 4 of JP-A-62-187253 of K. K. Inax, there is disclosed a sampling apparatus wherein a swing arm supporting an excrement sampling vessel is rotated along the bowl surface of a toilet bowl fixture to sample urine or other excrement. The bowl is provided at the rear part thereof with a cavity serving as a testing region, the excrement sampling vessel being moved after sampling into the testing region wherein excrement is subjected to analysis. After use, the sampling vessel is washed in the same rear region. This apparatus also requires a special purpose bowl fixture provided at the rear part with the testing region and also suffers from the disadvantage that a standard toilet bowl fixture cannot be used.

JP-A-3-139334 of Matsushita Denko K. K. discloses a urine sampling and analyzing apparatus having a wheeled main body which is intended to be pulled aside of the toilet bowl fixture when in use and to be moved away into a non-obstructive location such as the corner of the toilet room when not in use. The main body supports a urine sampling cup in a telescoping fashion so that, when urine is to be sampled, the urine sampling cup is moved into the bowl through a gap defined between the toilet bowl and the toilet seat. A testing strip is dipped into the urine sample sampled by the sampling cup and is tested for urinalysis.

The advantage of this apparatus is that urine can be sampled by using a standard-type toilet bowl fixture. However, the problem involved in this apparatus is that the wheeled main body as placed on the toilet floor occupies the toilet floor and therefore hinders cleaning of the toilet as well as routine use of the toilet for the purposes of excretion. Handling and manipulation of the apparatus is cumbersome because, each time the apparatus is used, the main body must be moved toward and away from the toilet bowl in order to position the apparatus in a non-obstructive location after use.

Furthermore, the position of the sampling cup is so high that the cup interferes with or comes too close to the body of the user as seated on the toilet seat because the sampling cup is inserted through the gap between the bowl and the toilet seat in the lateral direction to extend above the bowl. Moreover, the user must control the position of the main body of the apparatus by the hands to ensure that the sampling cup is properly positioned to meet the trajectory of falling urine. As a result, sampling of urine is extremely difficult to perform so that there is a risk of failure of sampling.

U.S. Pat. No. 4,636,474 to Ogura et al., JP-A-60-117155 of Toshiba K. K., and JP-U-1-136573 of Matsushita Denko K. K. disclose urinalysis apparatus wherein a swingable arm is mounted for pivoting movement to a toilet seat, with a urine sensor being arranged at the free end of the arm to analyze urine upon contact with urine excreted into the bowl. Similarly, JP-A-60-233551 of Matsushita Denki Sangyo K. K. discloses a urinalysis device which comprises a casing adapted to be hanged on the rim of the bowl fixture, an arm extending from the casing into the bowl, a spoon-shaped urine sampling vessel mounted to the end of the arm, and a urine sensor arranged in the sampling vessel. These apparatus also enjoy the advantage that they can be used in combination with the standard toilet bowl fixtures.

However, contacting the sensor directly with the original urine gives rise to several problems. Thus, in contrast to diagnosis by way of blood wherein the hydrogen ion concentration (pH), the chlorine ion concentration and the oxygen concentration are constantly conditioned to a high degree by various physiological organs, urine as an excrement from the human body is subject to a wide range of variations in the pH, the chlorine ion concentration and the oxygen concentration from sample to sample so that it is difficult to perform a high degree of analysis for a particular urinal constituent unless urine as sampled is diluted by a buffer. In addition, contacting the sensor directly with the original urine without dilution causes premature degradation of the sensor and reduces the service life thereof. Further, it is impossible to perform urinalysis for a plurality of items because it is difficult to arrange a plurality of sensors at the end of the swingable arm.

JP-U-5-30764 of NOK K. K. proposes a health diagnostic apparatus which is adapted to sample a quantity of urine by a urine sampling mechanism attached to a toilet seat and to transfer it to an analyzer station for urinalysis. In order to sample urine excreted from the user seated on the toilet seat by receiving it in mid air within the inner space of the toilet bowl, a swingable arm is pivoted at an end thereof to the underside of the toilet seat for swinging movement about a vertical axis, a vertically elongated tubular urine sampling cup being mounted to the other end of the arm. Urine sampled by the sampling cup is drawn by a manual or automatic syringe and, after being mixed with liquid reagent, is forwarded to the measuring station including an absorption spectrophotometer in which it is subjected to analysis.

This health diagnostic apparatus also enjoys the advantage of sampling urine by making use of a standard toilet bowl fixture without requiring a specially-fabricated toilet bowl fixture, since urine is sampled in mid air by the sampling cup which is moved within the inner space of the bowl. Furthermore, a high degree of analysis can be achieved as urine specimen is subjected to analysis after being diluted by the liquid reagent.

However, the problem of this apparatus is that it is difficult to effectively perform sampling of urine as excreted. More specifically, the direction of urination is subject to fluctuation depending on the difference in the sexuality of the user to the extent that in the case of a male the urine column tends to fall forwardly of the bowl along a relatively high trajectory in contrast to a female whose urine column tends to fall rather rearwardly of the bowl along a relatively low trajectory. In addition, the direction of urination varies from individual to individual so that the direction deviates each time depending on the posture of the user as seated on the toilet seat. As a result, the trajectory of the urine column falling into the bowl space of the toilet fixture tends to deflect in the vertical direction and the fore-and-aft direction as well as in the lateral direction. Accordingly, it is desirable that a urine sampling mechanism be capable of reliably and readily sampling urine regardless of any fluctuation in the trajectory of urine column that would result due to the sexual difference of the user or due to the variation in the posture of the user as seated on the toilet seat. This is particularly important when the total quantity of urine per urination is limited as is the case of elderly people who have increasing needs for urinalysis.

In order to sample urine without failure despite the occurrence of such a fluctuation in the trajectory of urine column, it would be desirable that the urine sampling vessel be made as large in size as possible. Otherwise, the chance of sampling would be lost if the urine column unfortunately fails to hit right on the sampling vessel. On the other hand, however, it is also desirable that, when not in use, the sampling vessel be readily stored in a non-obstructive place situated, for example, underneath the toilet seat, because the toilet must also be used for the purposes of routine excretion insofar as the urine sampling is performed by making use of a standard toilet fixture. To this end, therefore, another requirement imposed on the design of the urine sampling vessel is that it must be made sufficiently small in size and must be designed in such a form that facilitates storage. The urine sampling mechanism proposed in JP-U-5-30764 is difficult to meet with these opposing requirements because a cylindrical sampling cup elongated in the vertical direction is adopted.

Accordingly, the object of the present invention, broadly, is to provide a method and an apparatus for sampling urine at a toilet equipped with a conventional standard water closet bowl fixture.

More specifically, an object of the invention is to provide a method and an apparatus for sampling urine which are capable of sampling urine readily and without failure regardless of a fluctuation in the trajectory of urine column that would occur in the vertical, fore-and-aft or lateral direction due to the sexual difference of the user or due to the variation in the posture of the user as seated on the toilet seat.

Another object of the invention is to provide a method and an apparatus for sampling urine which are capable of effectively sampling urine while making use of a urine sampling vessel designed in such a form as to facilitate storage thereof when not in use.

A still another object of the invention is to provide a method and an apparatus for sampling urine which are capable of sampling urine without failure even when the user urinates with an easy posture.

A further object of the invention is to provide a method and an apparatus for sampling urine which do not hinder cleaning and routine use of the toilet.

DISCLOSURE OF THE INVENTION

The feature of the urine sampling method and apparatus according to the invention resides in that an elongated urine sampling trough of a U-shaped cross-section is used and that the sampling of urine is carried out with the sampling trough positioned in a vertical central plane of the bowl fixture in such a manner that it extends obliquely between the upper front region and the bottom region of the bowl space of the toilet bowl fixture. The urine sampling trough has a rearwardly and upwardly directed opening so as to receive urine ejected forwardly and downwardly from the user seated on the toilet seat. The urine sampling trough is provided at its lower end with a urine sump so as to recover urine flowing down along the sampling trough.

As in this manner the urine sampling trough is made elongated and is positioned obliquely between the upper front region and the bottom region of the inner space of the bowl, it extends for a considerable extent within the bowl inner space both in the vertical direction as well as in the fore-and-aft direction. Accordingly, even though the direction of urination is deviated in the vertical or fore-and-aft direction due to the difference in sexuality or posture of the user, the urine column will fall within the coverage of the length of the urine sampling trough so that the urine sampling trough is able to receive urine without failure.

In the event that the trajectory of urine is deviated in the lateral direction away from the vertical central plane of the bowl fixture., the urine sampling trough may be moved to the left or to the right, as required, with respect to the vertical central plane to bring the urine sampling trough in such a manner as to compensate for the lateral deviation of the urine trajectory.

Since in the urine sampling method and apparatus according to the invention, the urine sampling trough is adaptive in this manner to any vertical, longitudinal and lateral deviation of the urine column, sampling of urine can be carried out effectively while using an elongated or slender sampling trough. Consequently, urine may readily be sampled by making use of a standard toilet bowl fixture, without recourse to a special-purpose toilet bowl fixture wherein a sampling cavity is formed on the bowl surface for a wide surface area. Because the sampling trough is slender and elongated, it may readily be stored under the toilet seat when not in use.

In an embodiment of the urine sampling apparatus according to the invention, the urine sampling trough is supported at its upper end by the toilet seat for swinging movement about a generally horizontal axis located adjacent the front part of the rim of the bowl fixture and passing through the vertical central plane of the bowl fixture, the urine sampling trough being adapted to be driven by drive means, such as an electric motor, to oscillate about the horizontal axis between an operative position situated in the vertical central plane of the bowl fixture and a rest position situated adjacent the rim of the bowl fixture and located in a horizontal plane.

Preferably, the sampling trough is curved along the inner contour of the toilet seat. With this arrangement, the sampling trough when not in use will be concealed under the toilet seat upon rotation to a generally horizontal angular position. When the toilet seat is swung up for male's urination, the curved sampling trough will rotate conjointly with the toilet seat while it is snugly carried by the toilet seat.

The curved feature of the sampling trough also ensures that the sampling trough is moved closely to the curved inner surface of the bowl when oscillated in the inner space of the bowl. Therefore, there is no risk of the sampling trough to interfere with the body, particularly the penis, of the user seated on the toilet seat.

In a preferred embodiment of the invention, sampling of urine may be carried out while reciprocatingly oscillating the urine sampling trough for a predetermined angle with respect to the vertical angular position thereof. With such reciprocating movement, the sampling trough is able to better cover the lateral deviation of the urine column.

After use, the sampling trough may be washed with water under pressure ejected from a spray nozzle.

In another embodiment of the urine sampling apparatus according to the invention, the urine sampling trough is swingably mounted to the rim of the bowl fixture.

These features and advantages of the invention, as well as other features and advantages thereof, will become apparent from the following description made with reference to the preferred embodiments thereof.

BEST MODE FOR CARRYING OUT THE INVENTION

Figure 1:
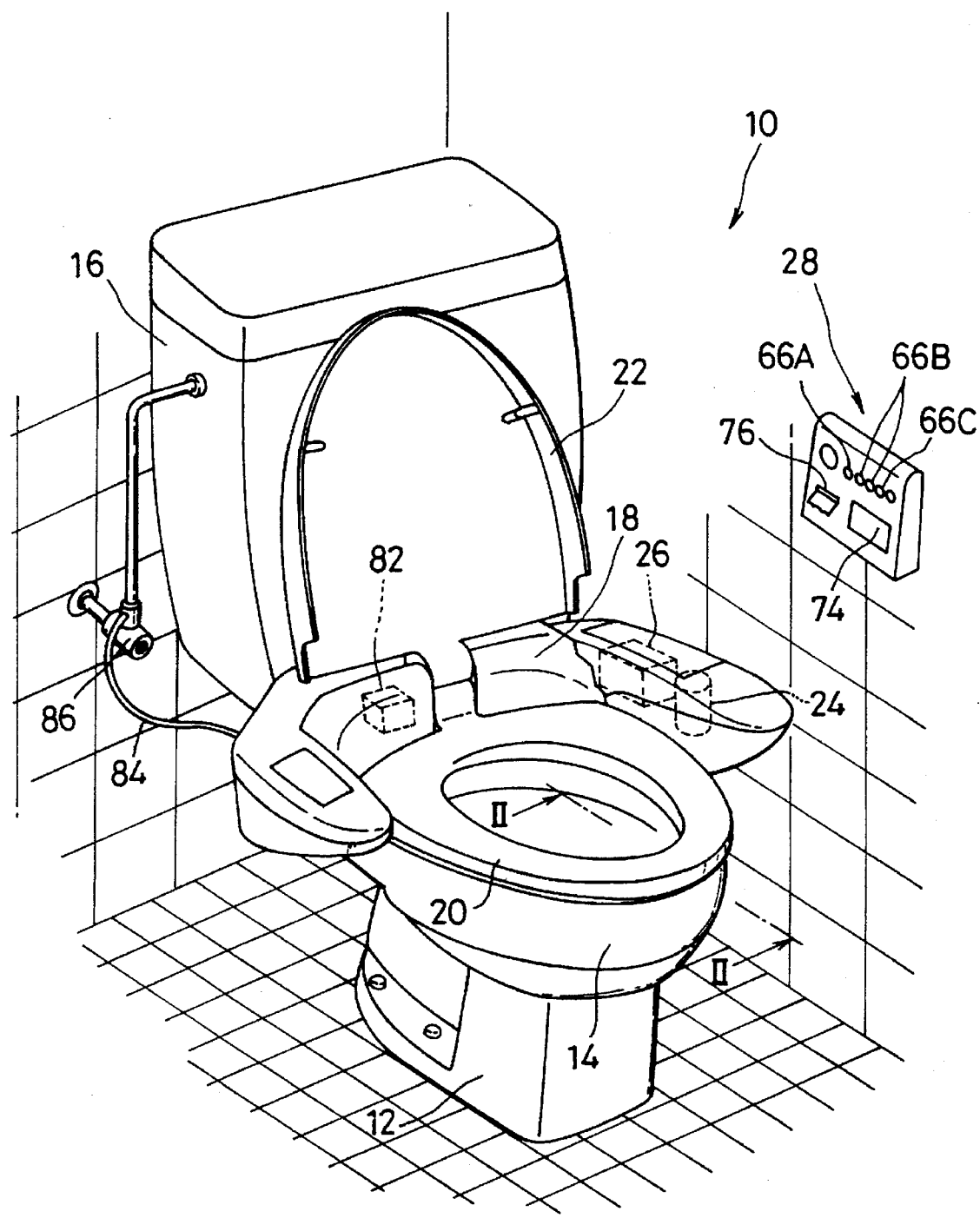
FIG. 1 is a perspective view of a toilet equipped with the urine sampling apparatus according to the invention.

The urine sampling method and apparatus according to the invention will now be described in more detail with reference to the accompanying drawings. Referring first to FIG. 1, the toilet 10 is provided with a commercially available, standard-type water closet bowl fixture 12 which is installed on the toilet floor in the conventional manner. The toilet bowl fixture 12 may be of any conventional one, including vortex type, siphon type, siphon jet type, and wash-downtype. The bowl fixture 12 has a conventional bowl 14 and a flushing water supply device, such as a cistern 16, arranged rearwardly of the bowl in the conventional manner. A housing 18 is secured to the bowl fixture 12 and a toilet seat 20 and a toilet lid 22 are swingably hinged to the housing 18.

The housing 18 receives a urine sample transfer pump, such as a syringe pump 24, and a urinalysis device 26, which are adapted to transfer urine sample recovered by the urine sampling apparatus of the invention toward the urinalysis device 26 and to subject it to urinalysis. As the syringe pump 24 and the urinalysis device 26 do not form part of the invention, they need not be described. A control unit 28 for controlling the urine sampling apparatus, the transfer pump 24 and the urinalysis device 26 may be installed on the side wall of the toilet.

Figure 2:
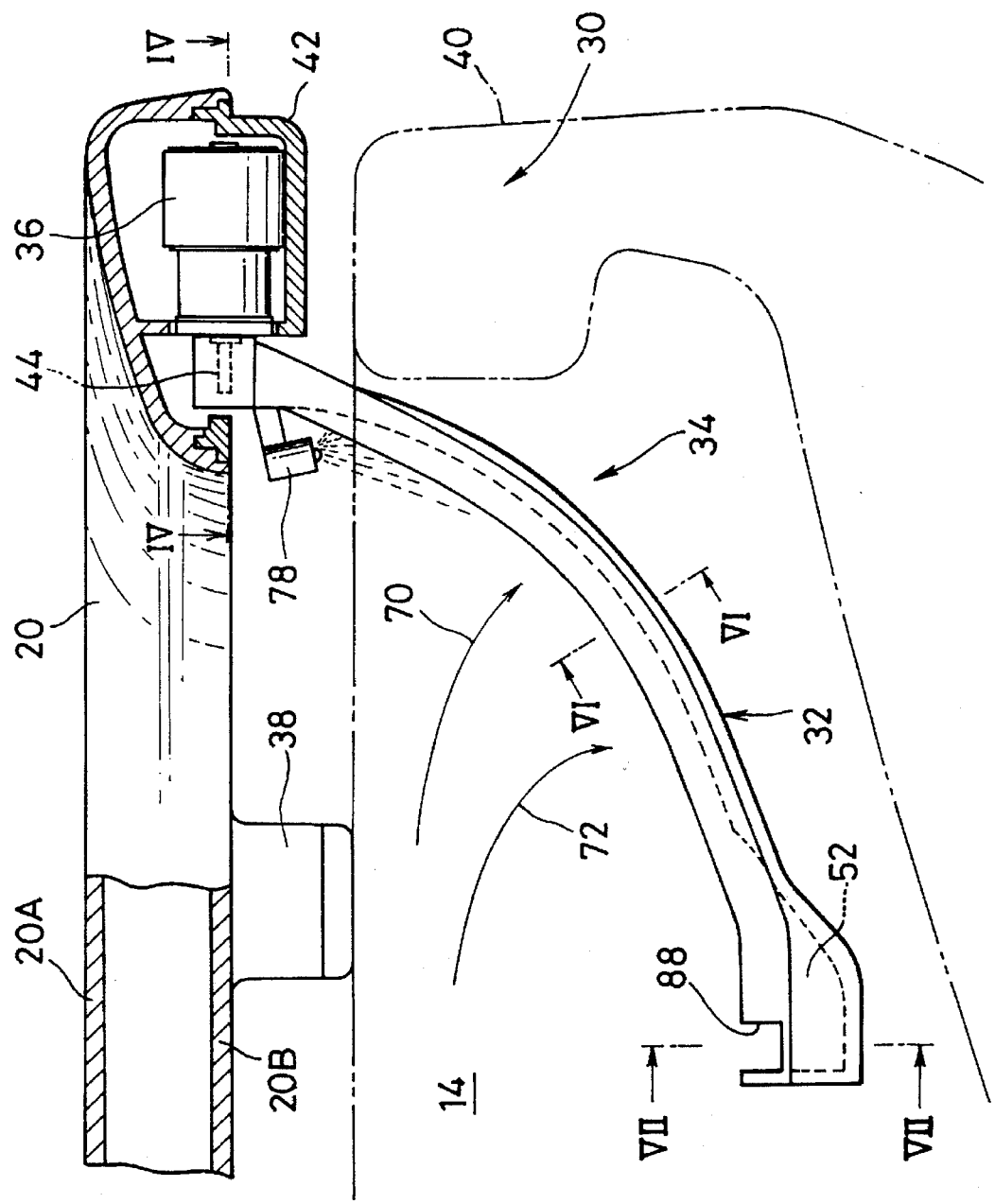
FIG. 2 is a cross-sectional view taken along the line II—II of FIG. 1 and showing the urine sampling apparatus according to the first embodiment of the invention.
Figure 3:
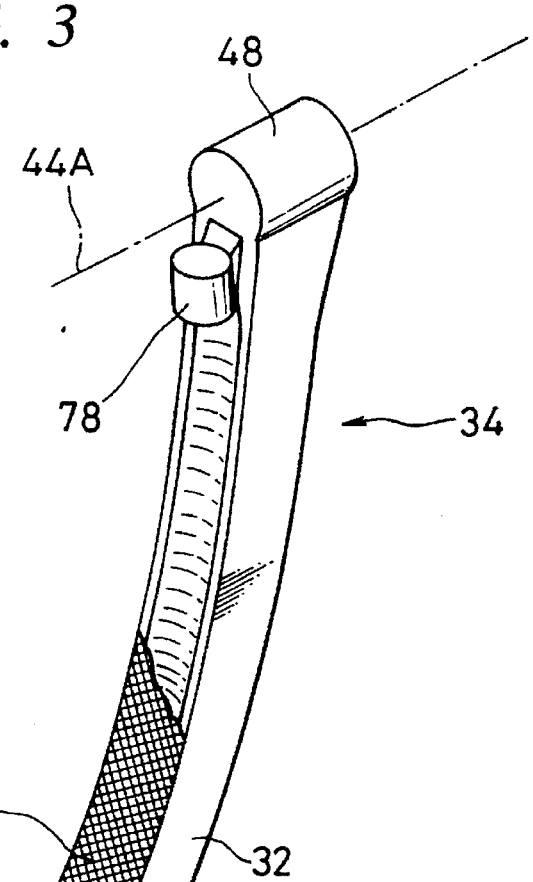
FIG. 3 is a perspective view of the urine sampling trough shown in FIG. 2, with a screen being cut out to show only a part thereof.
Figure 4:
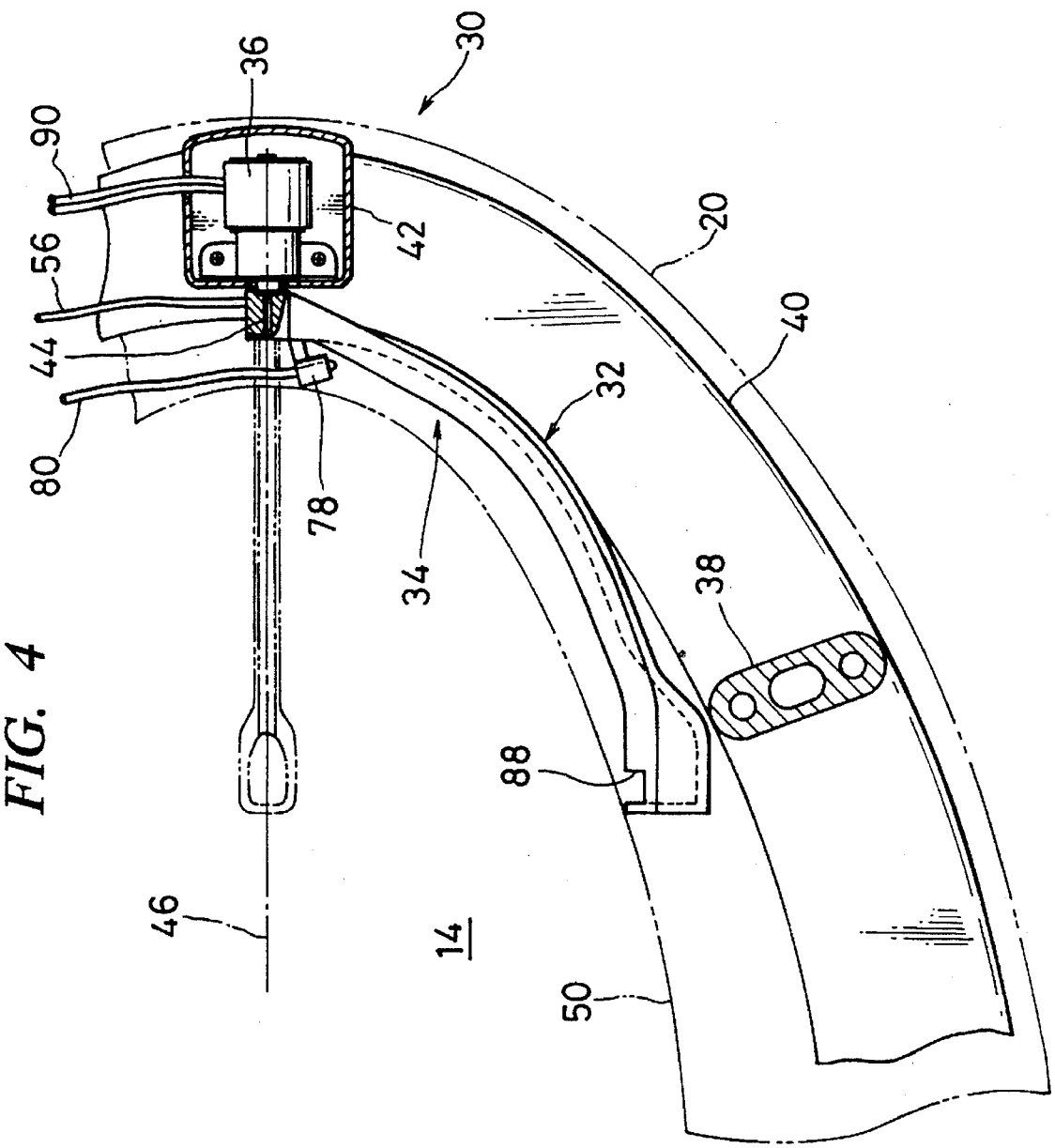
FIG. 4 is cross-sectional view, partly cut away, taken along the line IV—IV of FIG. 2, with the sampling trough as rotated to the horizontal and vertical positions being shown by the solid and phantom lines, respectively.

In FIGS. 2–8, there is shown the urine sampling apparatus according to the first embodiment of the invention. As shown in FIGS. 2 and 4, the urine sampling apparatus 30 of the invention is mounted to the toilet seat 20 and includes a swing arm 34, provided with an elongated urine sampling trough 32, and a geared stepping motor 36, with a reduction gear mechanism, which is controlled by the control unit 28 in such a manner as to oscillate the swing arm.

As best shown in FIG. 2, the toilet seat 20 may be formed of an upper half 20A and a lower half 20B of an impact resistive plastic material which are joined together, for example, by high-frequency fusion bonding. The toilet seat 20 is supported on the upper surface of a rim 40 of the bowl fixture 12 in the conventional manner by way of four legs, one of which is indicated at 38.

At the frontal part of the toilet seat 20, the lower half 20B of the toilet seat is formed with a downwardly bulged support section 42 to which the motor 36 is suitably secured. The output shaft 44 of the motor 36 has a horizontal axis 44A which passes the vertical central plane 46 of the bowl fixture 12 and which is situated adjacent the upper surface of the frontal part of the rim 40. The upper end of the swing arm 34 is provided with a hub 48 having an axial bore, not shown. The hub is keyed or otherwise splined to the output shaft 44 of the motor 36 so that the sampling trough 32 is oscillated together with the swing arm 34 within the inner space of the bowl 14 in response to the rotation of the motor 36.

As best shown in FIG. 4, the sampling trough 32 is curved along the inner contour 50 of the toilet seat 20 to ensure that, when rotated into a horizontal position, the sampling trough is situated inwardly of the inner periphery of the rim 40 and is concealed by the toilet seat 20. As will be apparent from FIGS. 3, 6 and 7, the urine sampling trough 32 has a U-shaped cross-section and has an inlet aperture which is open generally rearwardly and upwardly.

Figure 8:
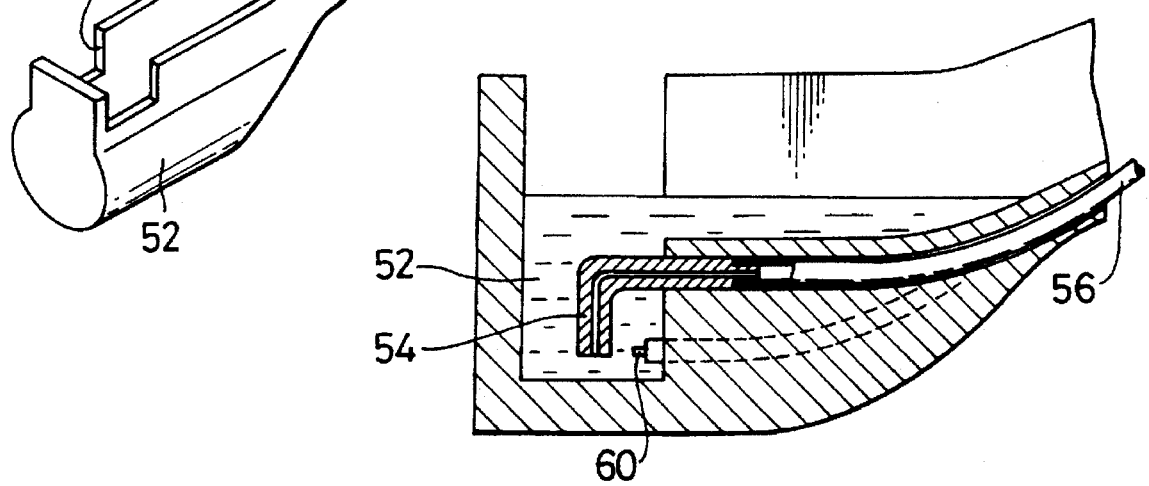
FIG. 8 is a cross-sectional view taken along the line VIII—VIII of FIG. 7.
Figure 7:
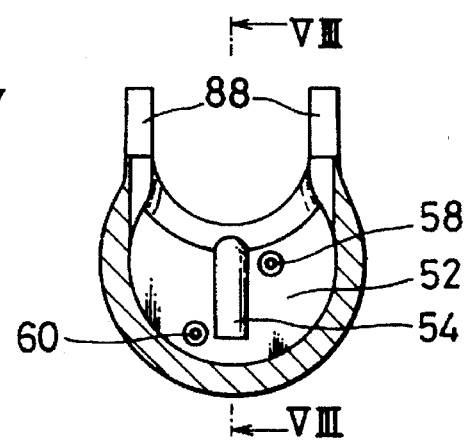

A small urine sump or receptacle 52 is provided at the lower end of the urine sampling trough 32. As shown in FIGS. 7 and 8, an L-shaped urine suction tube 54 is opened into the lower part of the urine sump 52 so that urine accumulated in the urine sump 52 is picked up from the bottom of the sump without accompanying air bubbles. The suction tube 54 is connected through a urine sample transfer tube 56 to the syringe pump 24 arranged in the housing 18 so as to transfer urine sample to the urinalysis device 26.

Figure 6:
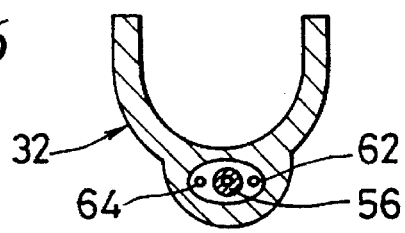
FIGS. 6 and 7 are cross-sectional views taken along the lines VI—VI and VII—VII, respectively, of FIG. 2.

A pair of vertically spaced electrodes 58 and 60 are exposed in the urine sump 52 and are connected to the control unit 28 via respective lead wires 62 and 64 shown in FIG. 6. The control unit 28 may be designed to apply a predetermined potential between the electrodes 58 and 60 and to detect accumulation of fresh urine in the urine sump 52 by monitoring the electric conductivity of a fluid being present between the electrodes 58 and 60 in accordance with the potential drop.

The control unit 28 is provided with a urinalysis start switch 66A. The control unit 28 is so programmed that, when the user presses upon the start switch, the motor 36 is driven to initially bring the urine sampling trough 32 into the vertical angular position shown by the solid line in FIG. 5. The control unit 28 may also be provided with fine adjustment switches 66B which are operable to position the sampling trough 32 in any desired angular position which is laterally offset from the vertical position as shown by the phantom line in FIG. 5.

Figure 5:
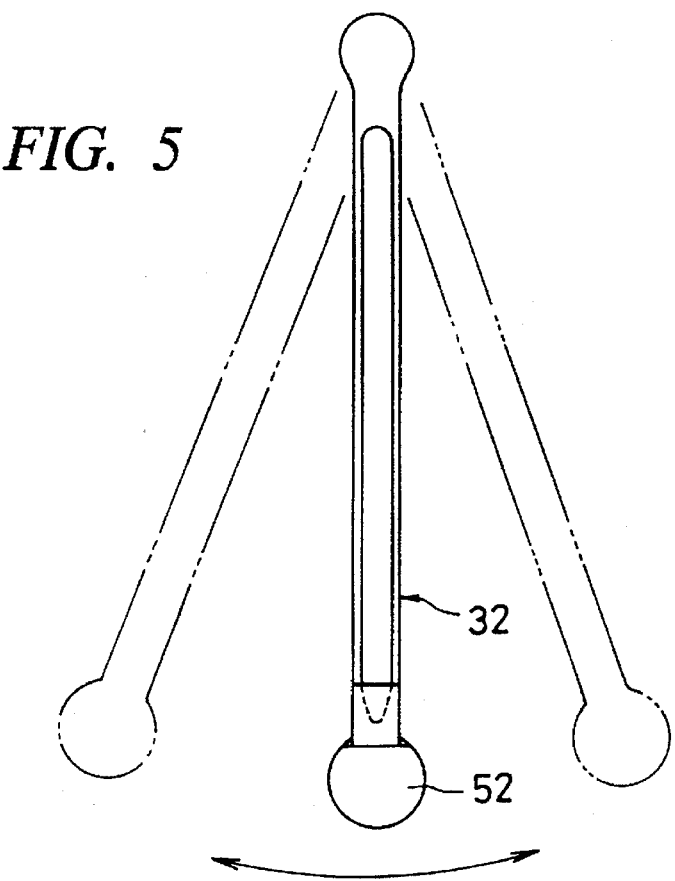
FIG. 5 is a rear elevational view of the sampling trough.

To describe the mode of operation and use of the urine sampling apparatus 30, as the user seated on the toilet seat 20 depresses the start switch 66A, the control unit 28 drives the motor 36 until the urine sampling trough 32 is rotated from the horizontal position indicated by the solid line in FIG. 4 to the vertical position shown in FIGS. 2 and 5. The user may then press on either of the fine adjustment switches 66B to finely adjust the angular position of the sampling trough 32 to the right or left as shown by the phantom line in FIG. 5.

As the user urinates with the sampling trough held in this position, urine impinging upon the sampling trough 32 will flow down along the sampling trough 32 to accumulate in the urine sump 52. The inlet opening of the sampling trough 32 is preferably covered with a meshed screen 68 made of a corrosion resistive material such as stainless steel to prevent urine impinging on the sampling trough 32 from splashing backwards and to prevent foreign material from entering the sampling trough.

It will be noted that, generally, the trajectory or locus of urine is susceptible to fluctuation depending on the difference in the sexuality of the user so that in the case of a male the urine column tends to fall relatively forwardly of the bowl along a relatively high trajectory as shown by the arrow 70 in FIG. 2, in contrast to a female whose urine column tends to fall on the bottom region of the bowl along a relatively low trajectory as shown by the arrow 72. However, since the sampling trough 32 is held to extend obliquely for a considerable extent between the front upper region and the bottom central region of the inner space of the bowl 14, the urine column always comes to intersect with the length of the sampling trough 32 even if the trajectory of urine column is deviated in the vertical or fore-and-aft direction. As in this manner the urine sampling trough 32 provides a large extent of coverage, it is able to receive urine at a high probability regardless of the difference in sexuality or posture of the user. If in addition the angular position of the sampling trough 32 is finely adjusted in the lateral direction, it will be easier to cause the urine column to hit upon the sampling trough 32.

The control unit 28 may further be provided with another switch 66C to ensure that upon depressing the switch 66C the sampling trough 32 is reciprocatingly oscillated laterally for a predetermined angle with respect to the adjusted position, as shown in FIG. 5. With such reciprocating motion, the elongated sampling trough 32 will traverse the falling urine column at a high probability so that urine is picked up each time the sampling trough 32 intersects the urine column.

Upon sensing that urine has accumulated in the urine sump 52 up to the level of the upper electrode 58, the control unit 28 operates the syringe pump 24 in the housing 18 to cause urine sample to be drawn from the urine sump 52 for transfer to the urinalysis device 26. As the suction tube 54 is opened into the bottom of the urine sump 52, only such urine sample that is free from air bubbles is transferred to the urinalysis device. The urine sample is subjected to urinalysis by the urinalysis device 26 and the control unit 28 displays the results of urinalysis on a display 74 and outputs it through a printer 76 in response to the instructions of the user.

As sampling of urine is completed in this manner, the sampling trough 32 and the urine sump 52 are washed with water. To this end, a water spray nozzle 78 is provided on the swing arm 34 at the top of the sampling trough 32 and is connected through a water supply tube 80 to a solenoid valve 82 (FIG. 1) arranged in the housing 18. The solenoid valve 82 is connected through a hose 84 to a branch adapter 86 connected to a water line so as to admit supply of tap water. Upon completion of sampling and transfer of urine, the control unit 28 signals the solenoid valve 82 to open to cause the spray nozzle 78 to eject water toward the sampling trough 32 thereby to wash the sampling trough 32 and the urine sump 52.

As the sampling trough 32 is thus cleansed, the control unit 28 drives the motor 36 so as to rotate the sampling trough 32 back to the generally horizontal stand-by position shown by the solid line in FIG. 4. The sampling trough 32 is provided at its lower end with recesses 88 so that water in the urine sump 52 is drained into the bowl 14 as the sampling trough 32 is rotated to the horizontal position. The sampling trough 32 may be rotated until it abuts against the lower face of the toilet seat 20. In this position, the sampling trough 32 is concealed under the toilet seat 20 as shown in FIG. 4, because the sampling trough 32 is curved along the inner contour of the toilet seat. Accordingly, the sampling trough does not hinder routine use of the toilet. Advantageously, the urine sampling apparatus 30 is rotated integrally with the toilet seat 20 as it is mounted to the toilet seat.

The urine sample transfer tube 56, the washing water supply tube 80, lead wires 90 for the motor 36, and the lead wires 62 and 64 may be arranged to extend along the underside of the toilet seat 20 to the housing 18 as shown in FIG. 4.

Figure 9:
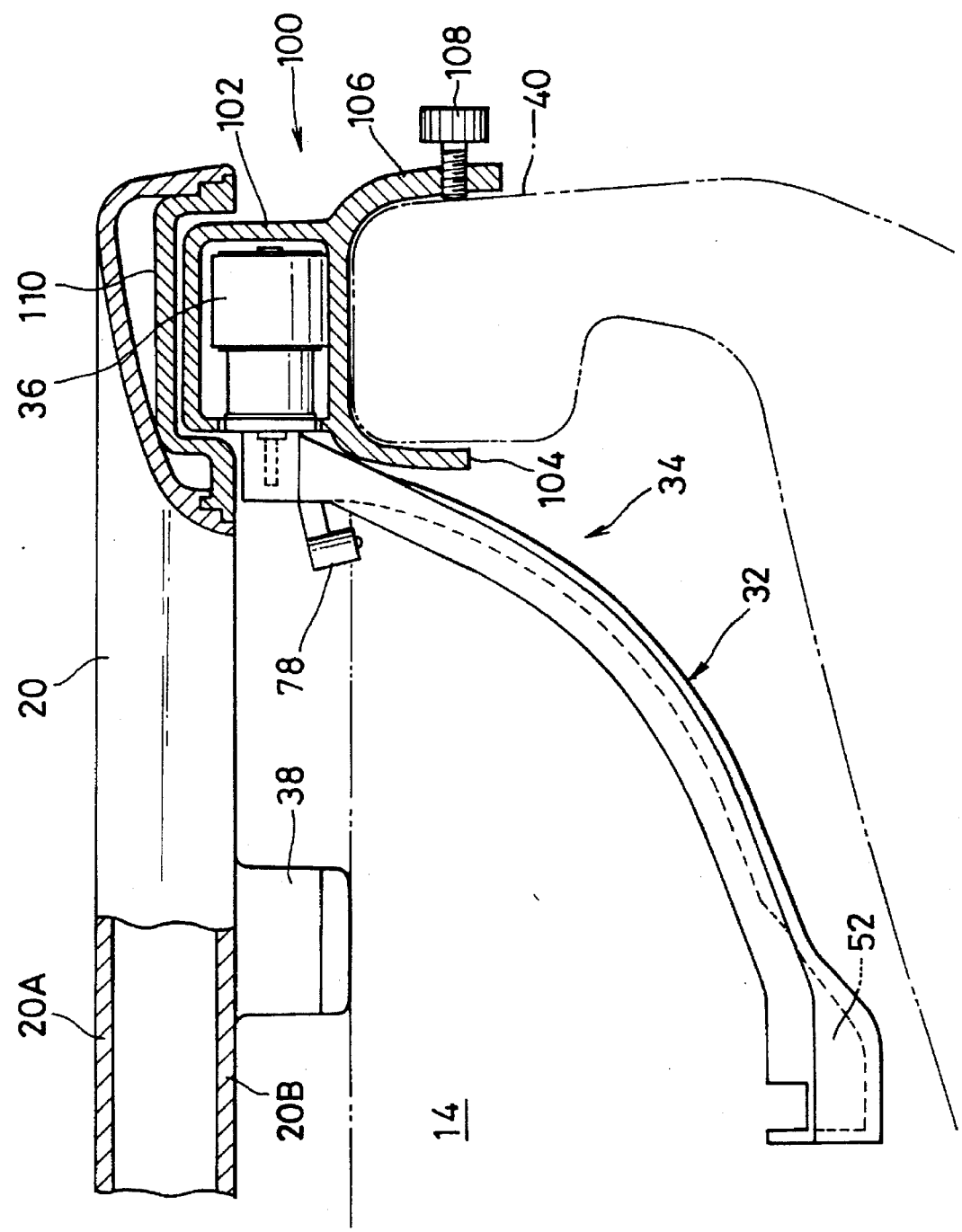
FIG. 9 is a cross-sectional view similar to FIG. 2 but showing the urine sampling apparatus according to the second embodiment of the invention.

FIG. 9 illustrates the urine sampling apparatus according to the second embodiment of the invention. The feature of this embodiment is that the urine sampling apparatus is adapted to be detachably mounted to the rim of the toilet bowl fixture. Parts and members similar to those of the first embodiment are indicated by like reference numerals and will not be described again. To describe only the difference, the motor 36 of the urine sampling apparatus 100 is secured to a box-like frame 102. The swing arm 34 having the urine sampling trough 32 is mounted to the output shaft of the motor 36 in a manner similar to the foregoing embodiment.

The frame 102 has a pair of extensions 104 and 106 striding over the rim 40 of the bowl fixture, with a screw 108 being threadingly engaged with the outer extension 106. The lower half 20B of the toilet seat 20 is provided with a concavity 110 corresponding to the frame 102 to ensure that the toilet seat does not interfere with the frame 102 when the toilet seat is rotated to its operative position. The urine sampling apparatus 100 may be readily fixed to the toilet bowl fixture by placing the frame to stride over the rim 40 of the bowl fixture as shown, followed by fastening the screw 108. The mode of use of the sampling apparatus is similar to that of the foregoing embodiment.

While the present invention has been described herein with reference to the specific embodiments thereof, it is contemplated that the present invention is not limited thereby and various changes and modification may be made therein. For instance, the cross-section of the urine sampling trough may be altered as required.

We claim:

1. An apparatus for sampling urine excreted by an individual seated on a toilet seat at a toilet equipped with a standard water closet bowl fixture, said apparatus comprising:

an elongated urine sampling trough having an elongated opening;

support means for supporting said sampling trough for swinging movement, about a generally horizontal axis located adjacent the front part of a rim of said bowl fixture and passing through the vertical central plane of said bowl fixture, between an operative position, in which said sampling trough extends in said vertical central plane obliquely between the upper front region and the bottom region of the inner space of the bowl and in which said opening is directed rearwardly and upwardly, and a rest position in which said sampling trough is situated adjacent the rim of said bowl fixture; and, drive means for swinging said sampling trough about said axis between said operative and rest positions.

2. An apparatus for sampling urine according to claim 1, wherein said support means is mounted detachably to the rim of said bowl fixture.

3. An apparatus for sampling urine according to claim 1, wherein at least part of said drive means is accommodated within said toilet seat.

4. An apparatus for sampling urine according to claim 1, wherein said support means is mounted to said toilet seat.

5. An apparatus for sampling urine according to claim 1, wherein said drive means is operable to reciprocate said sampling trough slightly on both sides of the vertical central plane of said bowl fixture.

6. An apparatus for sampling urine according to claim 1, wherein said drive means includes an electric motor.

7. An apparatus for sampling urine according to claim 1, wherein said sampling trough is curved along the inner contour of said toilet seat so that said sampling trough is substantially concealed by said toilet seat in said rest position.

8. An apparatus for sampling urine according to claim 1, wherein said apparatus comprises cleansing means for washing said urine sampling trough after use.

9. An apparatus for sampling urine according to claim 8, wherein said cleansing means comprises a water spraying nozzle directed toward said opening of said sampling trough.

10. An apparatus for sampling urine according to claim 1, wherein a urine sump is provided at the lower end of said sampling trough to recover urine flowing down along said sampling trough.

11. An apparatus for sampling urine according to claim 10, wherein said apparatus comprises a urine sample suction tube opened into the lower part of said urine sump.

12. An apparatus for sampling urine according to claim 10, wherein said apparatus comprises means for detecting that urine has accumulated in said urine sump to a predetermined level.

13. An apparatus for sampling urine according to claim 10, wherein said apparatus comprises means for discharging the content of said sampling trough into said bowl when said sampling trough is in said rest position.

14. An apparatus for sampling urine according to claim 1, wherein at least part of said opening of said sampling trough is covered by a meshed screen.

* * * * *